United States Patent [19]

Feiring

[11] 4,258,225
[45] Mar. 24, 1981

[54] TAF₅ AND NBF₅ AS FLUORINATION CATALYSTS

[75] Inventor: Andrew E. Feiring, Wilmington, Del.

[73] Assignee: E. I. Du Pont de Nemours and Company, Wilmington, Del.

[21] Appl. No.: 824,729

[22] Filed: Aug. 15, 1977

[51] Int. Cl.³ .............................................. C07C 17/08
[52] U.S. Cl. .................................... 570/168; 570/170
[58] Field of Search .......................... 260/653.6, 653.7

[56] References Cited

U.S. PATENT DOCUMENTS

| | | | |
|---|---|---|---|
| 2,005,710 | 6/1935 | Daudt et al. | 260/653.7 |
| 2,724,004 | 11/1955 | Frederick | 260/653 |
| 3,003,003 | 10/1961 | McGinty | 260/653.6 |
| 3,862,995 | 1/1975 | Martens et al. | 260/653.6 |

FOREIGN PATENT DOCUMENTS 675615 12/1963 Canada .

*Primary Examiner*—Delbert E. Gantz
*Assistant Examiner*—Joseph A. Boska

[57] ABSTRACT

A halogenated alkene is reacted with HF in the presence of TaF₅ or NbF₅ to produce a fluorinated alkane. Exemplary is the reaction of tetrachloroethene with HF in the presence of TaF₅ to produce 1,2,2-trichloro-1,1-difluoroethane and 1,1,2,2-tetrachloro-1-fluoroethane.

11 Claims, No Drawings

TAF$_5$ AND NBF$_5$ AS FLUORINATION CATALYSTS

BACKGROUND OF THE INVENTION

1. Field of the Invention

The invention concerns the reaction of a halogenated olefin having at least two halogen atoms attached to the olefinic carbons with HF in the presence of TaF$_5$ or NbF$_5$ to produce a fluorinated alkane.

2. Prior Art

U.S. Pat. No. 2,439,299 issued Apr. 6, 1948 to R. S. Hovey shows a fluorination reaction wherein TiF$_4$ is a catalyst and the starting material is a halogenated alkane.

U.S. Pat. No. 2,560,838 issued July 17, 1951 to R. C. Arnold discloses boron trifluoride as a catalyst to promote the addition of anhydrous HF to olefinic compounds such as tetrachloroethylene.

U.S. Pat. No. 2,724,004 granted Nov. 15, 1955 to M. R. Frederick shows SbCl$_5$ or SbF$_3$Cl$_2$ as fluorination catalysts for the reaction of tetrachloroethylene with HF.

Canadian patent 675,615 issued Dec. 10, 1963 discloses the use of a fluoride of a metal of the group vanadium, chromium, manganese, iron, cobalt, nickel, titanium and silver as a fluorination catalyst.

V. A. Legasov et al. in Russian Journal of Inorganic Chemistry 17 (9) 1256-58 (1972) show the reaction of xenon difluoride with carbon tetrachloride in the presence of TaF$_5$.

Chem. Abstracts 77, 4863 w (1972) shows the use of NbF$_5$ and I$_2$ in converting tetrafluoroethene to pentafluoroethyl iodide.

The processes of the prior art where a halogenated olefin is used as starting material and BF$_3$ or SbCl$_5$ are used as catalysts are deficient in that the yield of the more highly fluorinated alkanes is not as high as could be desired. Also, these catalysts require special handling since BF$_3$ is a gas and SbCl$_5$ is a fuming, highly hygroscopic liquid. The latter also has a relatively short catalyst life since it readily converts to inactive SbCl$_3$.

DESCRIPTION OF THE INVENTION

In contrast, the catalysts of the instant invention are easily handled crystalline solids, which have the additional advantage of favoring the production of the more highly fluorinated alkanes than do the prior art catalysts.

The invention can be described as the process of contacting at a temperature of 0° C. to 200° C. under substantially anhydrous conditions, one molar equivalent of a halogenated olefin of the formula $$R_1R_2C=CR_3R_4$$

wherein
R$_1$ is H, F, Cl, CH$_3$, CCl$_3$ or CF$_3$;
R$_2$ is H, F or Cl;
R$_3$ is H, F or Cl;
R$_4$ is F or Cl;
in which at least two of the R groups are F or Cl; with 1 to 8 molar equivalents of HF and in the presence of 0.01 to 0.25 molar equivalents of TaF$_5$ or NbF$_5$ to produce a fluorinated alkane.

The halogenated olefin starting materials of the invention do not react with hydrogen fluoride alone under the conditions of temperature and pressure used in this invention and require the presence of the catalysts. The preferred halogenated olefins are tetrachloroethene, trichloroethene, dichloroethene and trichlorofluoroethene, the first two of which are most preferred because of their commercial availability, ease of use in the invention, and because the fluorinated products obtained from them are useful as refrigerants, solvents and blowing agents.

The catalysts are commercially available crystalline solids and can be used alone or on a support such as carbon. TaF$_5$ is preferred since it is more active in producing the more highly fluorinated products and also in converting a higher proportion of the starting material to products.

The reaction can be carried out at from 0° C. to 200° C. In liquid-phase reactions, when R$_1$, R$_2$, R$_3$ and R$_4$ are F or Cl, the preferred temperature range is from 75° C. to 200° C., and when one or two of R$_1$, R$_2$ or R$_3$ is H, the preferred temperature range is from 0° C. to 70° C. At reaction temperatures below these limits the reaction becomes too slow to be useful, and at temperatures above these limits the yield of product is lowered by side reactions and polymerization.

The process is believed to occur in two stages:

(a) Initially, one mole of hydrogen fluoride adds to the olefinic bond of the substrate, e.g., $$CCl_2=CCl_2 + HF \rightarrow CHCl_2CCl_2F \quad (1)$$

(b) Subsequently, one or more chlorine atoms of this adduct may be replaced by fluorine atoms as the reaction proceeds, e.g., $$CHCl_2CCl_2F + HF \rightarrow CHCl_2CClF_2 + HCl \quad (2)$$

$$CHCl_2CClF_2 + HF \rightarrow CHCl_2CF_3 + HCl \quad (3)$$

The addition of hydrogen fluoride to the carbon-carbon double bond of the halogenated olefin is a stoichiometric reaction in which one mole of hydrogen fluoride is required for each mole of olefinic substrate. It is advantageous to use an excess of hydrogen fluoride to make the addition reaction go to completion; up to 8.0 moles of hydrogen fluoride per mole of olefin may be used; the preferred amount is from 1.1 to 1.5 moles of hydrogen fluoride per mole of olefin.

As the concentration of hydrogen fluoride adduct increases with time in the reaction mixture, substitution reactions occur in which one or more chloride atoms of the adduct are replaced by fluorine atoms. The introduction of each of the subsequent fluorine atoms requires a further mole of hydrogen fluoride per mole of substrate undergoing substitution. Stoichiometrically, the process could continue until either all the chlorine in the substrate or all the hydrogen fluoride is consumed.

Anhydrous or substantially anhydrous conditions means that water, which is detrimental to the reaction, should be excluded as much as possible from the reaction zone. The HF which is commercially available as anhydrous grade has so little water, about 0.5% or less, that is can be used in the reaction directly. The halogenated olefins and the catalysts also contain little or no water and can similarly be used directly. Exclusion of moisture from the reaction vessel by means of appropriate moisture traps, etc., is a routine procedure and is well known in the art.

The reaction can be carried out in liquid phase or vapor phase and at autogenous pressures. Both the liquid phase and vapor phase processes include batch, semicontinuous and continuous modes of operation.

For liquid phase reactions, the amount of catalyst used is from 0.01 to 0.25 moles per mole of halogenated olefin starting material, and is preferably from 0.025 to 0.09 moles per mole of olefin.

For vapor phase reactions, it is convenient to support the TaF$_5$ or NbF$_5$ on an inert porous material such as carbon or other known supports to ensure even distribution of the catalyst in the reaction zone. The catalyst should be replenished from time to time because TaF$_5$ and NbF$_5$ are sufficiently volatile at temperatures above 150° C. to be carried over in the product stream by evaporation. The amount of TaF$_5$ or NbF$_5$ to inert support is from 10% to 50%, with amounts of about 25% being preferred.

The reaction vessel is constructed from materials which are resistant to the action of hydrogen fluoride; examples include metal alloys such as Hastelloy and plastics such as polyethylene, polypropylene, polychlorotrifluoroethylene, and polytetrafluoroethylene. For reactions at temperatures either below the boiling point of hydrogen fluoride (19.5° C.) or below the boiling point of the most volatile halocarbon reactant, the reaction vessel can be closed or open to the atmosphere if provisions to exclude moisture are taken. For reactions at temperatures at or above the boiling point of hydrogen fluoride or the most volatile component, a closed vessel is used to minimize the loss of reactants.

Pressure is not critical. Atmospheric and autogeneous pressures are the most convenient and are therefore preferred. Means can be provided for the venting of excess pressure of hydrogen chloride formed in the substitution reaction and can offer an advantage in minimizing the formation of side products.

In general, the reactions are conducted by introducing the reagents in any order into the reaction vessel. Generally, the catalyst and halo-olefin are placed in the reaction vessel which is then cooled, and the required amount of hydrogen fluoride is condensed in the vessel. The vessel may be evacuated prior to the introduction of hydrogen fluoride and cooled in dry ice or liquid nitrogen to facilitate collection of the hydrogen fluoride. The contents of the vessel are raised to the appropriate reaction temperature and agitated by shaking or stirring for a length of time sufficient to cause the reaction to occur. The reaction time and temperature necessary for the desired reaction to occur can be determined by monitoring the composition of aliquots of the reaction mixture. Each aliquot is dissolved in dichloromethane, quenched with sodium fluoride, and analyzed by well-known techniques, such as gas-liquid chromatography (glpc, preferred method), fluorine nuclear magnetic resonance spectroscopy ($^{19}$F nmr), and proton nuclear magnetic resonance spectroscopy ($^1$H nmr). The reaction time can be from 1 to 17 hrs; the preferred reaction times are from 1 to 6 hours.

In the vapor phase reaction, the reactants are introduced into the reactor above their boiling points. The temperature of the reactor must also be sufficient to keep the products of the reaction in the vapor state so that they pass over into a cooled receiver beyond the reactor rather than remain in the catalyst zone for a prolonged period of time. Generally, the vapor-phase reaction temperatures are between 100° C. and 200° C., with 170°–180° C. preferred. The contact time of the reagents with the catalyst may be specified instead of reaction time. The combined operations of feed rate, control of reactor temperature and pressure, and rate of removal of product from the reactor influence the residence time of the product in the reactor. It may be desirable to shorten the residence time for a given product within the reactor to control the formation of side products. Contact time is the average time that the reactant-product mixture is in contact with the catalyst. Broadly, contact times of from 0.1 to 25 sec. are useful in the process of the invention, with preferred contact times in the range of 1 to 10 sec.

The products are isolated by any of a variety of well-known techniques. The contents of the reaction vessel can be discharged onto ice, the organic layer collected, washed with water and dried with a drying agent such as calcium chloride. The product may be purified by distillation and analyzed by the usual techniques such as gas-liquid chromatography, NMR spectroscopy or mass spectrometry.

The fluorinated alkanes produced by the invention have utility as refrigerants, solvents and blowing agents. They can also be used as starting materials for the preparation of other useful compounds. For example, 1,1,2,2-tetrachloro-1-fluoroethane may be dehydrochlorinated to trichlorofluoroethene (O. Paleta and A. Posta, *Collect. Czech. Chem. Commun.*, 33, 1294 (1968), British Pat. No. 723,715, Feb. 9, 1955). 1,1,1-Trifluoro-2,2-dichloroethane may be used to prepare trifluoroacetyl chloride (German Pat. No. 2,418,676, Nov. 14, 1974). The mono- and difluorinated compounds produced by this process can also be used as intermediates to prepare more highly fluorinated compounds.

SPECIFIC EMBODIMENTS OF THE INVENTION

In the following illustrative examples all parts and percentages are by weight and all temperatures are Centigrade unless otherwise stated. All reactions used anhydrous HF and were carried out with the exclusion of water.

Fluorine nuclear magnetic resonance ($^{19}$F nmr) chemical shifts ($\delta$) are in parts per million from internal fluorotrichloromethane, and proton nuclear magnetic resonance (nmr) chemical shifts ($\delta$) are in parts per million from internal tetramethylsilane; the solvent was deuteriochloroform (CDCl$_3$) unless otherwise stated. The density of liquid hydrogen fluoride at 19.5° C. is 0.991 g ml$^{-1}$, so volume or weight can be used practically interchangeably in measuring quantities of this reagent. Gas-liquid phase chromatography (glpc) conditions are specified within the individual examples.

EXAMPLE 1

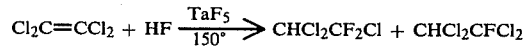

An 80-ml Hastelloy bomb tube was charged with 33.2 g (0.2 mole) of tetrachloroethene and 5.0 g (0.018 mole) of tantalum pentafluoride (Alfa Inorganics). The bomb was cooled in dry ice and acetone, evacuated and charged with 10 g (0.5 mole) of commercial anhydrous hydrogen fluoride, and brought to atmospheric pressure with nitrogen. The bomb was agitated for six hours with an inside temperature of 150°. The bomb was cooled in ice water and the contents were discharged onto 30 g of ice, using 40 ml of water to rinse the bomb. The lower organic layer was collected, washed with water and dried over anhydrous calcium chloride. The material weighed 24.9 g. The product was analyzed by gas liquid chromatography against authentic comparison samples. Analysis of the product using a 10 ft×0.25 in 10% Carbowax column with an oven temperature of 60° and a helium carrier gas flow of 60 ml/min showed the following products with their relative percentages: 1,2,2-trichloro-1,1-difluoroethane (92.7), 1,1,2,2-tetrachloro-1-fluoroethane (4) and unreacted tetrachloroethane (3.3). Analysis of the product by gas chromatography with an oven temperature of 120° C. showed a trace amount of pentachloroethane in addition to these products.

EXAMPLE 2

The procedure of Example 1 was duplicated using 1.4 g (0.005 mole) of tantalum pentafluoride instead of 5.0 g (0.018 mole). Gas chromatographic analysis of the product (27.3 g) showed the presence of the following products with their relative percentages: 1,2,2-trichloro-1,1-difluoroethane (94), 1,1,2,2-tetrachloro-1-fluoroethane (3), 2,2-dichloro-1,1,1-trifluoroethane (1.7) and unreacted tetrachloroethene (1.2).

EXAMPLE 3

The procedure of Example 1 was duplicated except that the bomb tube was agitated at 75° for 6 hr. Gas chromatographic analysis of the product (30.3 g) showed the presence of the following products and their relative percentages: 1,2,2-trichloro-1,1-difluoroethane (29.6), 1,1,2,2-tetrachloro-1-fluoroethane (39.7) and unreacted tetrachloroethene (30.7).

EXAMPLE 4

The procedure of Example 1 was duplicated except that 2.8 g (0.011 mole) of tantalum pentafluoride was used and the bomb tube was agitated at 150° C. for 1 hr. Gas chromatographic analysis of the product (26.9 g) showed the presence of the following products with their relative percentages: 1,2,2-trichloro-1,1-difluoroethane (95.8), 2,2-dichloro-1,1,1-trifluoroethane (2.3), 1,1,2,2-tetrachloro-1-fluoroethane (1.5) and unreacted tetrachloroethene (0.5).

EXAMPLE 5

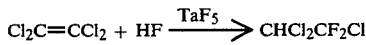

A 360-ml Hastelloy bomb tube was charged with 132.8 g (0.8 mole) of tetrachloroethene and 5.6 g (0.02 mole) of tantalum pentafluoride. The bomb was cooled in dry ice and acetone, evacuated and charged with 40 g (2 mole) of hydrogen fluoride. The bomb was agitated for 6 hr with an inside temperature of 150°. The bomb was cooled in ice water and the contents were discharged onto 50 g of ice using 75 ml of water to rinse the bomb. The lower organic layer was separated, washed with water and dried over calcium chloride. It weighed 126.5 g. A 115.6-g portion of the product was distilled at atmospheric pressure to give 104.6 g (0.675 mole, 84%) of 1,2,2-trichloro-1,1-difluoroethane as a colorless liquid, bp 70°–72°. It was identified by: proton NMR (δ, neat) 5.85 (t, J=5.3 Hz); fluorine NMR (δneat) −63.31 (d, J=5.3 Hz).

EXAMPLE 6

The procedure of Example 1 was followed except that the amount of hydrogen fluoride was increased to 20 g (1.0 mole) and the amount of tantalum pentafluoride was decreased to 2.8 g (0.01 mole). The contents of the bomb tube were transferred to an evacuated 100-ml Hoke cylinder which was cooled in dry ice and acetone. The volatile materials were carefully vented at this temperature, and the remaining contents were treated with 30 ml of water and separated. The lower organic layer (25.9 g) showed a major signal at δ5.84 ppm (t, J=5.3 Hz) in the proton NMR spectrum, which is characteristic of 1,2,2-trichloro-1,1-difluoroethane. Gas chromatographic analysis of the product confirmed the presence of the following components and their relative percentages: 1,2,2-trichloro-1,1-difluoroethane (92), 1,1,2,2-tetrachloro-1-fluoroethane (5) and unreacted tetrachloroethene (3).

EXAMPLE 7

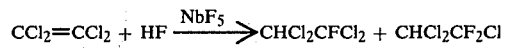

The procedure of Example 1 was duplicated using 1.88 g (0.01 mole) of niobium pentafluoride as catalyst in place of the tantalum pentafluoride. Gas chromatographic analysis of the product (29.0 g) showed the presence of the following products with their relative percentages: 1,2,2-trichloro-1,1-difluoroethane (4), 1,1,2,2-tetrachloro-1-fluoroethane (34) and unreacted tetrachloroethene (61). Fluorine NMR showed absorptions at −63.32 ppm for 1,2,2-trichloro-1,1-difluoroethane and −61.31 ppm for 1,1,2,2-tetrachloro-1-fluoroethane.

EXAMPLE 8

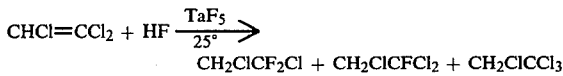

A 50-ml vessel constructed from polychlorotrifluoroethylene was incorporated into a vacuum line and charged with 0.6 g (0.0022 mole) of tantalum pentafluoride. The vessel was evacuated and cooled in liquid nitrogen. Hydrogen fluoride (5 g, 0.25 mole) and trichloroethene (10.5 g, 0.08 mole) were distilled into the vessel. The resulting mixture was stirred at 25° for 2 hr. Pressure in the vessel was maintained at 12–16 psi. The volatile materials in the reaction vessel were vacuum distilled into a second polychlorotrifluoroethylene vessel which contained 40 g of cracked ice and was cooled in liquid nitrogen. The mixture in the trap was allowed to melt. After separation, the lower organic layer was washed with water and dried over anhydrous calcium chloride. It weighed 8.5 g. The product was analyzed by gas chromatography against authentic comparison samples, using a 10 ft×¼ in 10% Carbowax column with an oven temperature of 50° and a helium carrier gas flow of 60 ml/min. The products detected (relative percentages) were 1,2-dichloro-1,1-difluoroethane (41), 1,1,2-trichloro-1-fluoroethane (57) and 1,1,1,2-tetrachloroethane (2). Proton NMR showed signals at δ4.14 ppm (d J=13 Hz) for CH$_2$ClCClF$_2$ and 3.98 ppm (t J=11 Hz) for CH$_2$ClCFCl$_2$.

EXAMPLE 9

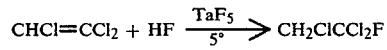

A 250-ml polychlorotrifluoroethylene vessel was charged with 2.2 g (0.008 mole) of tantalum pentafluoride. The vessel was evacuated, cooled in liquid $N_2$ and charged by distillation with 20 g (1.0 mole) of hydrogen fluoride. The vessel was filled with nitrogen and immersed in a bath of water and ethylene glycol at 5°. Trichloroethene (108 g, 0.8 mole), cooled to 0° C., was added in one portion. The resulting mixture was stirred for 2.5 hr. The mixture was poured over 40 g of cracked ice. The organic layer was separated, washed with water, and dried over anhydrous calcium chloride. It weighed 116.7 g. 1,1,2-Trichloro-1-fluoroethane (108.1 g, 89%), bp 87°–89° was obtained by distillation; the proton NMR spectrum of this compound shows a doublet (J=13 Hz) at δ4.13.

EXAMPLE 10

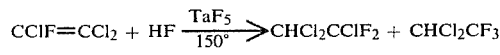

$$CClF=CCl_2 + HF \xrightarrow[150°]{TaF_5} CHCl_2CClF_2 + CHCl_2CF_3$$

The procedure of Example 1 was followed using 30 g (0.2 mole) of trichlorofluoroethene, 10 g (0.5 mole) of hydrogen fluoride and 5.0 g (0.018 mole) of tantalum pentafluoride. Gas chromatographic analysis of the product (23.9 g) showed the presence of the following products and their relative percentages: 1,2,2-trichloro-1,1-difluoroethane (80) and 2,2-dichloro-1,1,1-trifluoroethane (20) in agreement with fluorine NMR signals at δ−63.38 ppm (d) for $CHCl_2CClF_2$ and −78.60 ppm (d) for $CHCl_2CF_3$.

EXAMPLE 11

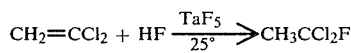

$$CH_2=CCl_2 + HF \xrightarrow[25°]{TaF_5} CH_3CCl_2F$$

An 80-ml Hastelloy bomb was charged with 2.8 g (0.01 mole) of tantalum pentafluoride. The bomb was evacuated, cooled in dry ice and acetone and charged with 10 g (0.5 mole) of hydrogen fluoride and 38.8 g (0.2 mole) of 1,1-dichloroethene. The mixture was agitated for 3 hr at 25°. The contents of the bomb tube were transferred to an evacuated Hoke cylinder which was cooled in dry ice and acetone. The Hoke cylinder was connected to a vacuum line and the volatile contents were vacuum distilled into a 250-ml polychlorotrifluoroethylene vessel containing 40 g of cracked ice and cooled in liquid nitrogen. This mixture was allowed to melt. The lower organic layer was separated and washed with water to give 16.8 g of 1,1-dichloro-1-fluoroethane; proton NMR δ2.42 ppm (d, J=16.5 Hz). The nonvolatile residue in the Hoke cylinder was 11.9 g of dark oil which appeared to be a complex mixture from its NMR spectrum.

EXAMPLE 12

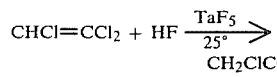

$$CHCl=CCl_2 + HF \xrightarrow[25°]{TaF_5} CH_2ClCClF_2 + CH_2ClCCl_2F + CH_2ClCCl_3$$

An 80-ml Hastelloy bomb tube was charged with 4.2 g (0.015 mole) of tantalum pentafluoride. This bomb tube was evacuated, cooled in dry ice and acetone and charged with 10 g (0.5 mole) of hydrogen fluoride and 39.5 g (0.3 mole) of trichloroethene. The bomb was agitated for 17 hr at 25°. The bomb contents were discharged over 40 g of ice using 40 ml of water as a rinse.

The organic layer was separated, washed with water and dried over anhydrous calcium chloride, yield 36 g of liquid. Gas chromatographic analysis as in Example 8 showed the presence of the following products and their relative percentages: 1,2-dichloro-1,1-difluoroethane (57), 1,1,2-trichloro-1-fluoroethane (21) and 1,1,1,2-tetrachloroethane (22).

EXAMPLE 13–31

The processes of the invention can be used to prepare the chlorofluorocarbons shown in the following table.

| Example No. | Starting Material | Products |
|---|---|---|
| 13 | CHCl=CHCl (cis or trans) | CH_2ClCHClF |
| 14 | CF_3CCl=CCl_2 | CF_3CHClCCl_2F<br>CF_3CHClCClF_2<br>(CF_3)_2CHCl |
| 15 | CF_3CH=CCl_2 | CF_3CH_2CCl_2F<br>CF_3CH_2CClF_2<br>(CF_3)_2CH_2 |
| 16 | CH_2=CF_2 | CH_3CF_3 |
| 17 | CF_2=CCl_2 | CF_3CHCl_2 |
| 18 | CClF=CF_2 | CHClFCF_3 |
| 19 | CF_2=CF_2 | CHF_2CF_3 |
| 20 | CHCl=CClF | CH_2ClCClF_2 |
| 21 | CHF=CCl_2 | CH_2FCCl_2F |
| 22 | CHF=CHF | CH_2FCHF_2 |
| 23 | CF_3CF=CF_2 | CF_3CHFCF_3 |
| 24 | CF_3CCl=CF_2 | CF_3CHClCF_3 |
| 25 | CCl_2FCF=CF_2 | CCl_2FCHFCF_3 |
| 26 | CFCl=CFCl (cis or trans) | CHClFCClF_2<br>CHClFCF_3 |
| 27 | CHCl=CF_2 | CH_2ClCF_3 |
| 28 | CHF=CClF | CH_2FCClF_2 |
| 29 | CHF=CF_2 | CH_2FCF_3 |
| 30 | CHF=CHCl (cis or trans) | CHF_2CH_2Cl |
| 31 | CH_2=CClF | CH_3CClF_2 |

To contrast the use of the prior art catalysts the following experiments were run.

EXAMPLE 32

$$CCl_2=CCl_2 + HF \longrightarrow CHCl_2CCl_2F + CHCl_2CClF_2$$

The procedure of Example 1 was followed in which separate reactions were carried out at 150° for 6 hr with the amounts of catalysts and products shown below. Each reaction was carried out with 33.2 g (0.2 mole) of tetrachloroethene and 10 g (0.5 mole) of hydrogen fluoride.

| Catalyst | Amount | % Conversion of Tetrachloroethene | Product Analysis* | |
|---|---|---|---|---|
| | | | CHCl_2CCl_2F | CHCl_2CClF_2 |
| TaF_5 | 1.4 g (0.005 mole) | 97 | 3 | 97 |
| SbCl_5 | 1.79 g (0.006 mole) | 51 | 59 | 41 |

*Relative percentages determined by glpc.

It is seen that in comparison with SbCl_5, TaF_5 not only gives better overall conversion of the unsaturated olefin to fluorinated products, but is more selective for the preparation of the more highly fluorinated product.

EXAMPLE 33

The procedure of Example 32 was repeated but using a temperature of 75°, with the amounts of catalysts and conversion to products shown below.

| Catalyst | Amount | % Conversion of Tetrachloroethene | Product Analysis* | |
|---|---|---|---|---|
| | | | $CHCl_2CCl_2F$ | $CHCl_2CClF_2$ |
| $TaF_5$ | 5.0 g (0.018 mole) | 70 | 57 | 43 |
| $SbCl_5$ | 5.4 g (0.018 mole) | 0 | 0 | 0 |

*Relative percentages determined by glpc.

With $SbCl_5$ as catalyst the desired reaction did not occur since only starting material was recovered. It is thus seen that tantalum pentafluoride catalyzes the reaction of HF with tetrachloroethene at a lower temperature than does $SbCl_5$.

Examples 32 and 33 therefore illustrate that $TaF_5$ is superior to $SbCl_5$ in requiring milder conditions, giving better yields, and being more selective in the hydrofluorination and chlorine-fluorine exchange reactions.

EXAMPLE 34

$$CHCl=CCl_2 + HF \longrightarrow CH_2ClCCl_2F + CH_2ClCClF_2$$

The procedure of Example 12 was followed in which separate reactions were carried out at 25° for 17 hr with 39.5 g (0.3 mole) of trichloroethene and 0.015 mole (5%) of $TaF_5$ and $BF_3$. The results are as shown.

| Catalyst | Amount | % Conversion of Trichloroethene | Product Analysis* | |
|---|---|---|---|---|
| | | | $CH_2ClCCl_2F$ | $CH_2ClCClF_2$ |
| $TaF_5$ | 4.2 g (0.015 mole) | 100 | 21 | 57 |
| $BF_3$ | 1.0 g (0.015 mole) | 32.8 | 100 | 0 |

*Relative percentages by glpc and proton NMR.

This example shows that $TaF_5$ promotes the complete conversion of the trichloroethene and that the major product is the difluorinated material whereas the reaction with $BF_3$ is incomplete and no difluorinated material is produced.

I claim:

1. The process of contacting under substantially anhydrous conditions at a temperature range of 0° to 200° C. one mole of a halogenated olefin of the formula $$R_1R_2C=CR_3R_4$$

wherein
$R_1$ is H, F, Cl, $CH_3$, $CCl_3$ or $CF_3$;
$R_2$ is H, F or Cl;
$R_3$ is H, F, or Cl;
$R_4$ is F or Cl;
in which at least two of the R groups are F or Cl; with 1 to 8 molar equivalents of HF and in the presence of 0.01 to 0.25 molar equivalents of $TaF_5$ or $NbF_5$ to produce a fluorinated alkane having one hydrogen atom over and above the number of hydrogen atoms originally present in the halogenated olefin.

2. The process of claim 1 in which the amount of HF is 1.1 to 1.5 moles.

3. The process of claim 1 in which the catalyst is $TaF_5$.

4. The process of claim 1 in which the catalyst in $NbF_5$.

5. The process of claim 1 in which the catalyst is $TaF_5$ in an amount of 0.025 to 0.09 molar equivalents.

6. The process of claim 1 in which the temperature is 75° to 200° C. when $R_1$, $R_2$, $R_3$ and $R_4$ are F or Cl.

7. The process of claim 1 in which the temperature is 0° to 70° C. when one of $R_1$, $R_2$ or $R_3$ is H.

8. The process of claim 1 in which the halogenated olefin is tetrachloroethene.

9. The process of claim 1 in which the halogenated olefin is trichloroethene.

10. The process of claim 1 in which the halogenated olefin is tetrachloroethene and the catalyst is $TaF_5$.

11. The process of claim 1 in which the halogenated olefin is trichloroethene and the catalyst is $TaF_5$.

* * * * *